United States Patent [19]
McHenry et al.

[11] Patent Number: 5,902,246
[45] Date of Patent: May 11, 1999

[54] METHOD AND APPARATUS FOR CALIBRATING AN OPTICAL PROBE

[75] Inventors: Peter McHenry, Needham, Mass.; Arthur E. Schulze, Houston, Tex.

[73] Assignee: LifeSpex, Incorporated, Kirkland, Wash.

[21] Appl. No.: 08/823,044

[22] Filed: Mar. 21, 1997

Related U.S. Application Data

[60] Provisional application No. 60/014,073, Mar. 26, 1996.

[51] Int. Cl.$^6$ ........................................................ A61B 5/00
[52] U.S. Cl. ......................... 600/476; 600/477; 356/243; 250/458.1
[58] Field of Search .................................... 600/310, 476, 600/477, 478; 356/39–42, 243; 250/458.1, 252.1

[56] References Cited

U.S. PATENT DOCUMENTS

| | | | |
|---|---|---|---|
| 4,476,870 | 10/1984 | Peterson et al. | 128/634 |
| 4,785,814 | 11/1988 | Kane | 128/634 |
| 5,414,258 | 5/1995 | Liang | 250/252.1 |
| 5,792,049 | 8/1998 | Eppstein et al. | |

*Primary Examiner*—Ruth S. Smith
*Attorney, Agent, or Firm*—David H. Carroll

[57] ABSTRACT

An optical body cavity probe (110, 310, 1200, 1300) is provided with a disposable flexible comformable sheath (120) having an optical window (220), or a disposable rigid sheath (320, 1210, 1310) having an optical window (420). The electronic system includes optical sources for generating the illuminating electromagnetic energy, filters or spectrum analyzers for isolating returned wavelengths of interest, and a computer for processing the returned wavelengths of interest to determine the tissue properties of interest as well as to calibrate the system. For calibration purposes, a removable calibration body (510, 910, 1010, 1220, 1330, 1430) bearing a fluorescence pattern resides on the outside of the optical window (500, 900, 1000, 1210, 1310, 1420) so as to be in the field of view of the probe when the sheath is installed over the probe. The calibration body is maintained in contact with the optical window during a calibration sequence using an adhesive, an endcap, shrink wrap material, or other suitable means. After the system is calibrated, the calibration body is removed and discarded and the investigation is begun. Once the investigation is completed, the sheath containing the optical window is removed, if present, and discarded.

24 Claims, 5 Drawing Sheets

METHOD AND APPARATUS FOR CALIBRATING AN OPTICAL PROBE

This application claims benefit of Provisional Appln. Ser. No. 60/014,073, filed Mar. 26, 1996.

BACKGROUND OF THE INVENTION

1. Field of the Invention

The present invention relates to a method and apparatus for calibrating an optical probe, and more particularly to a method and apparatus for calibrating an optical probe using a disposable calibration body.

2. Description of Related Art

Various optical probes are available for investigating properties of animal tissue in vivo and in vitro. In spectroscopy, various illuminating wavelengths are applied to the tissues of an animal body, typically through the probes but also through ambient light or through separate light sources. The probes receive optical activity resulting from application of the illuminating energy for detecting properties of the animal body. Typically, a probe is part of a diagnostic or screening system that includes electromagnetic sources for generating the illuminating energy, filters or spectrum analyzers for isolating wavelengths of interest, and computers for processing the wavelengths of interest to determine the tissue properties of interest.

System calibration is performed to minimize the impact of system variations and perturbations and to ensure the most accurate determinations possible. Calibration reduces the effects of variations in the dimensions and optical characteristics of different probes, compensates for drift and other instabilities over time in the electronic detection system caused by various environmental factors and aspects of the systems, including heat, humidity, voltage fluctuations, component aging, cable displacements, accumulated contamination, and the like, and compensates for various system and component failures.

One calibration technique used in fluorescent spectroscopy involves dipping the probe into a fluorescent solution such as Rhodamine, or placing the probe directly against a calibration cell containing the fluorescent solution. While generally effective for calibration purposes, the use of such liquids has several disadvantages which limit their usefulness for operational deployment in a clinical setting. Some of the fluorescent liquids raise safety and usage issues of toxicity, leakage, spillage, and the like. Some of the fluorescent liquids have a short lifetime and must be replaced on a preventive maintenance schedule or after each use. Where the probe is placed against a glass or plastic vial which contains the fluorescent liquid, measures must be taken to eliminate interference reflection and interaction with room lighting. Moreover, the result of calibrations with vials can be operator-dependent. Where the probe is immersed in the fluorescent liquid, calibration in the exam room involves awkward procedures.

Accordingly, methods and apparatus are desired that do not have the disadvantages of the liquid and vial calibration procedures.

SUMMARY OF THE INVENTION

Advantageously, the present invention simplifies and makes reliable calibration of optical probes.

One embodiment of the present invention is an optical probe apparatus that comprises an optical probe, a material body, and a support. The optical probe has an optical window that is transparent to optical energy at a first wavelength. The material body is interactive with the optical energy at a second wavelength to return optical energy at the first wavelength. The support removably disposes the material body in a field of view of the optical window. The interactive property is fluorescence in one variation, and is Raman scattering in another variation. In another variation, the apparatus further comprises a single use material supported by the substrate in the field of view of the optical window. In yet another variation, the apparatus further comprises an optical mask disposed about the field of view of the optical window. In yet another variation, the apparatus further comprises a code supported by the substrate in the field of view of the optical window.

Another embodiment of the present invention is an article of manufacture comprising a body containing fluorescent material distributed in a predetermined pattern across a region of the body. The fluorescent material is excitable by optical energy at a first wavelength to become fluorescent at a second wavelength in a predetermined pattern across the body region.

Yet another embodiment of the present invention is a method for calibrating a tissue analysis system that includes an optical probe having an optical window transparent to a return wavelength. In accordance with the method, a calibration body is positioned in a field of view of the optical window. Optical energy is applied to the calibration body, the optical energy interacting with material distributed in the calibration body to return energy at a return wavelength in a predetermined pattern across a region of the calibration body. The energy at the return wavelength is detected through the optical window in accordance with a set of scaling factors, and a decision is made whether the predetermined pattern is present from the energy detected in the detecting step. In the event that the predetermined pattern is found to be not present in the deciding step, the set of scaling factors is adjusted and the illuminating, detecting, and deciding steps are repeated. In a further embodiment, the illumination energy is applied through the same optical window used to detect the return wavelength, which is also transparent to the illumination energy. In yet a further embodiment, the probe is rejected as defective if certain criteria are not satisfied, such as, for example, if the predetermined pattern is not detected after a predetermined number of cycles through the adjusting, detecting, and deciding steps.

A further embodiment of the present invention is a method for calibrating a tissue analysis system that includes an optical probe having an optical window transparent to a return wavelength. In accordance with the method, a calibration body is positioned in a field of view of the optical window. The calibration body is illuminated at an illuminating wavelength to excite material distributed in the calibration body, the excited material emitting energy at a return wavelength in a predetermined pattern across a region of the calibration body. The energy at the return wavelength is detected through the optical window in accordance with a set of scaling factors, and a decision is made whether the predetermined pattern is present from the energy detected in the detecting step. In the event that the predetermined pattern is found to be not present in the deciding step, the set of scaling factors is adjusted and the illuminating, detecting, and deciding steps are repeated. In a further embodiment, the illumination energy is applied through the same optical window used to detect the return wavelength, which is also transparent to the illumination energy. In yet a further embodiment, the probe is rejected as defective if certain criteria are not satisfied, such as, for example, if the predetermined pattern is not detected after a predetermined number of cycles through the adjusting, detecting, and deciding steps.

BRIEF DESCRIPTION OF THE DRAWINGS

In the drawings, in which like reference characters indicate like parts.

DETAILED DESCRIPTION OF THE PREFERRED EMBODIMENT(S)

Figure 1:
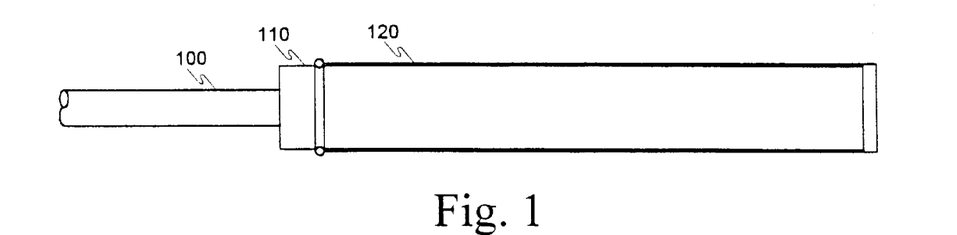
FIG. 1 is a side view of an optical body cavity probe on which a disposable sheath is installed.

The calibration techniques described herein are suitable for a variety of probe designs, including probes designed for in vivo or in vitro applications, surface or subsurface measurement, and biopsy probes, for example. FIG. 1 shows, for example, an optical body cavity probe 110 on which a disposable sheath 120 is installed. Illustratively, the probe 110 is similar to the type described in U.S. patent application Ser. No. 08/415,356, filed on Mar. 31, 1995 for "Optical Probe for the Detection of Cervical Neoplasia Using Fluorescence Spectroscopy and Apparatus Incorporating Same" and naming Richards-Kortum et al. as inventors, which is hereby incorporated herein by reference in its entirety. Illustratively, the probe 110 is a slightly tapered cylindrical tube approximately seven inches in length, and is of a diameter suitable for cervical investigation, typically from about 0.5 inches to 1.5 inches in diameter.

The probe 110 is connected to an electronic system (not shown) by an optical cable 100. The electronic system includes optical sources for generating the illuminating electromagnetic energy, filters or spectrum analyzers for isolating returned wavelengths of interest, and computers for processing the returned wavelengths of interest to determine the tissue properties of interest. For example, exemplary in vivo and in vitro systems and methods for using various electromagnetic wavelengths to detect cancers and precancers of the cervix using auto-fluorescence and Raman spectroscopy are described in various patent documents, including U.S. Pat. No. 5,421,339, issued Jun. 6, 1995 to Ramanujam et al. and entitled "Diagnosis of Dysplasia Using Laser Induced Fluoroescence" [sic], which is hereby incorporated herein by reference in its entirety; U.S. patent application Ser. No. 08/412,325, filed Mar. 31, 1995 for "Optical Method for the Detection of Cervical Neoplasias Using Fluorescence Spectroscopy"60 and naming Richards-Kortum et al. as inventors, which is hereby incorporated herein by reference in its entirety; U.S. patent application Ser. No. 08/403,446, filed Mar. 14, 1995 for "Optical Method and Apparatus for the Diagnosis of Cervical Precancers Using Raman and Fluorescence Spectroscopies" and naming Richards-Kortum et al. as inventors, which is hereby incorporated herein by reference in its entirety; U.S. patent application Ser. No. 08/666,021, filed Jun. 19, 1996 for "Diagnostic Method and Apparatus for Cervical Squamous Intraepithelial Lesions in vitro and in vivo Using Fluorescence Spectroscopy" and naming Richards-Kortum et al. as inventors, which is hereby incorporated herein by reference in its entirety; and U.S. patent application Ser. No. 08/667,993, filed Jun. 19, 1996 for "Near-Infrared Raman Spectroscopy for in vitro and in vivo Detection of Cervical Precancers" and naming Richards-Kortum et al. as inventors, which is hereby incorporated herein by reference in its entirety. It will be appreciated that other probe designs permit other techniques such as electrical cabling or wireless communications to be used to communicate information between the probe and the electronic system. For example, one alternative design incorporates some of the optical systems into the probe.

Figure 2:
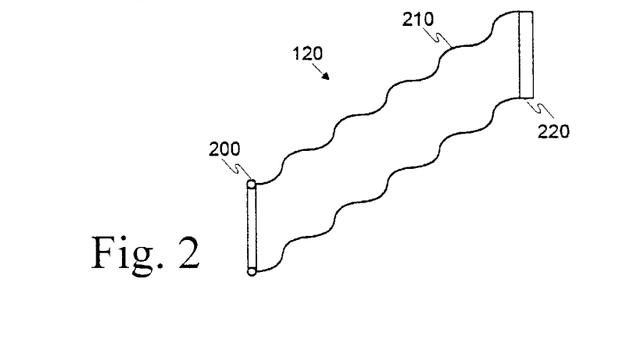
FIG. 2 is a side view of the disposable sheath of FIG. 1.

The sheath 120 is shown in isolation in FIG. 2. The sheath 120 is made of a flexible and preferably thin-walled tubular member 210, which is designed to be conformable with the probe 110. The tubular member 210 has a retainer member 200 at one end and a reasonably liquid-impermeable optical window 220 at the other end, and preferably is made of a resilient, reasonably liquid-impermeable, and non-toxic material such as nitrile, rubber or latex. The retainer member 200 illustratively is a thickened portion of the same material having a diameter just slightly smaller than the diameter of the probe 110. The optical window 220 is of any suitable non-toxic material having optical properties that do not adversely affect the detection methods, such as fused glass, silica, quartz, or optical plastic. Illustratively, the optical window 220 is a thin transparent disk to which the tubular member 210 is bonded. Alternatively, the optical window 220 is a shaped portion of the tubular member 210. Unless resilient and designed to assume the shape of the optical end of the probe 110, the optical window 220 is of any desired shape, although preferably the inside surface conforms to the optical end of the probe 110 and the outside surface conforms to the shape of the surface to be examined by the probe 110. The optical window 220 may have no optical effect or may be a lens having a predetermined focal property, a variable focal property, or a confocal property.

The sheath 120 is prepackaged and sterilized if desired. The sheath 120 is installed on the probe 110 by urging the resilient retaining member 200 over the body of the probe 110 until the retaining member 200 engages an annular surface depression about the body of the probe 110. At this time, the tubular member 210 is slightly stretched and pulls the optical window 220 firmly against an optical window (not shown) at the end of the probe 110.

Figure 3:
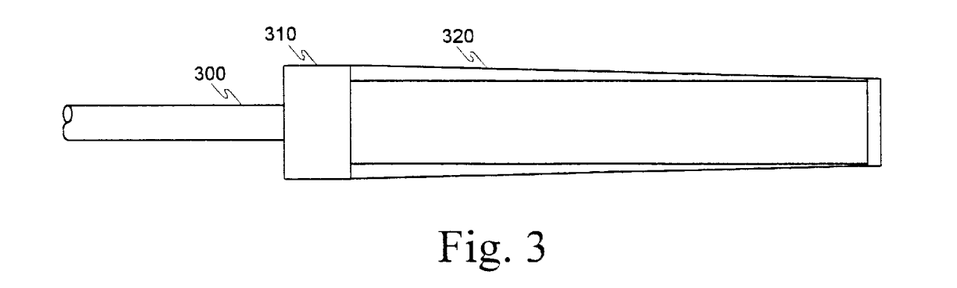
FIG. 3 is a side view of an optical body cavity probe on which an alternative disposable sheath is installed.

FIG. 3 shows an optical body cavity probe 310 on which a disposable sheath 320 is installed, resulting in a unit having a slightly tapered cylindrical form approximately seven inches in length, and of a diameter suitable for cervical investigation, typically from about 0.5 inches to 1.5 inches in diameter. The probe 310 is connected to an electronic system (not shown) by an optical cable 300.

Figure 4:
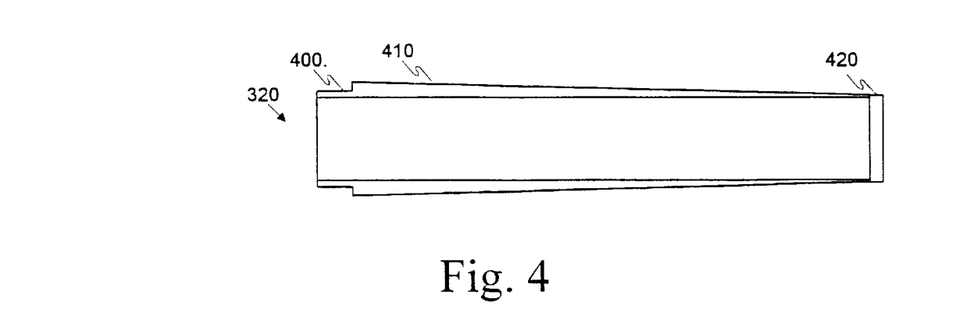
FIG. 4 is a side view of the alternative disposable sheath of FIG. 3.

The sheath 320 is shown in isolation in FIG. 4. The sheath 320 is made of a rigid and substantially tubular member 410 having a retainer member 400 of reduced diameter at one end and a reasonably liquid-impermeable optical window 420 at the other end. The tubular member 410 slightly tapers toward the optical window 420. The sheath 320 is molded from a preferably rigid, reasonably liquid-impermeable, reasonably shatter-resistant, and non-toxic material such as plastic. Alternatively, the sheath 320 may comprise assembled components. For example, tubular member 410 may be of any suitable non-toxic rigid material such as plastic, metal or glass, and the optical window 420 is attached to the end of the tubular member 310 with any suitable adhesive, for example. The optical window 420 may be made of any suitable non-toxic rigid material formed to any desired shape and having optical properties that do not adversely affect the detection methods, such as fused glass, silica, quartz, or optical plastic. If used with an elongated probe such as the probe 110, the is optical window 420 may be of any suitable transparent non-toxic resilient material designed to assume the shape of the optical end of the probe 110. The optical window 420 may have no optical effect or may be a lens having a predetermined focal property, a variable focal property, or a confocal property.

The sheath 320 is prepackaged and sterilized if desired. Illustratively, the sheath 320 is installed on the probe 310 by slipping the sheath 320 over the end of the probe 310 and urging the sheath 320 toward the enlarged diameter portion of the probe 310 until the reduced diameter portion 400 enters into a corresponding slot in the enlarged body portion of the probe 310. The sheath 320 is twisted to engage the probe 310, and may be disengaged from the probe 310 with a twist in the opposite direction. This retainer mechanism is commonly known as a bayonet connector, although any one of a variety of other retainer designs may be used as well.

Figure 5:
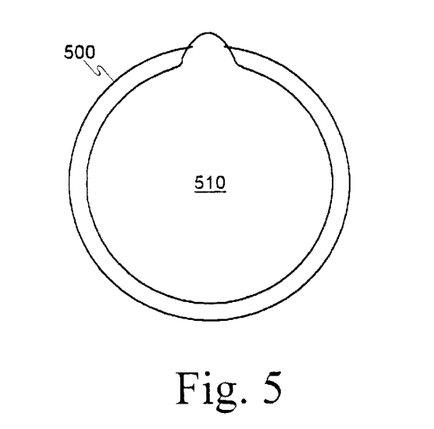
FIGS. 5 and 6 are front and cross-sectional views respectively of a calibration body disposed on an optical window.
Figure 6:
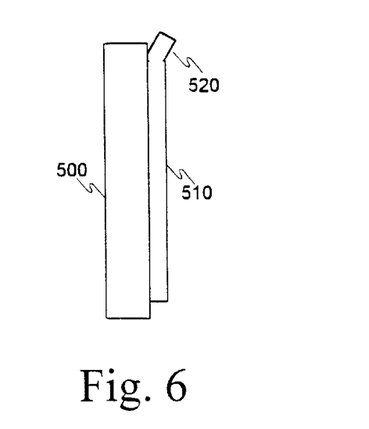

For calibration purposes, a removable calibration body resides preferably on the outside of the optical window, e.g., optical windows 220 or 420 of sheaths 120 and 320, so as to be in the field of view of the optical probe, e.g., optical body cavity probe 110 or 310, when a sheath is installed over the probe, and removable therefrom. For example, FIGS. 5 and 6 show an optical window 500 that is illustratively representative of an optical window such as 220 or 420 or any other suitable portion of a sheath, whether rigid or pliable. The optical window 500 is designed to be positioned over the optical window of an optical probe, and is transparent or essentially transparent to the illuminating and return wavelengths used in the detection method. In addition, the optical window 500 may, if desired, be endowed with other properties such as the ability to reflect or absorb particular wavelengths other than the wavelengths used in the detection method. Where the optical window of the probe is rigid, the optical window 500 preferably is placed against the optical window of the probe. Where the optical window of the probe is an orifice or a membrane, the optical window 500 preferably is suspended in the field of view of the optical window of the probe. A calibration body 510 is disposed preferably on the optical window 500, and is maintained in contact with the optical window 500 during a fluorescence spectroscopy calibration sequence. The calibration body 510 bears a fluorescence pattern. The exact fluorescence pattern is not critical, provided it is know to the calibration system. The sheath preferably is furnished with the calibration body 510 in place on the optical window 500, and the whole assembly is sterilized if necessary. All materials used in the sheath, including the optical window 500 and the calibration body 510, preferably are capable of withstanding sterilization by at least one of the generally well known and widely accepted manufacturing sterilization methods, with gamma sterilization being the preferred method. After the system is calibrated, the calibration body 510 is removed and discarded and the investigation is begun. Once the investigation is completed, the sheath containing the optical window 500 is removed and discarded.

In an alternative technique, a calibration body (not shown) like the calibration body 510 is disposed against the optical window of an optical probe using any suitable retention means, including a sheath that contains the calibration body in place of an optical window, or is disposed on the inside of an optical window of a sheath. In either case, the system is calibrated with the calibration body in position within the field of view of the probe, after which the calibration body is removed and discarded. A sterile sheath having an optical window is placed over the probe and the investigation is begun. Once the investigation is completed, the sheath is removed and discarded. While this technique is also advantageous for calibration, it does involves additional steps relative to the earlier described technique.

It will be appreciated that the calibration body can be retained against the optical window of the probe using other techniques as well. For example, typically a probe is protected during shipping by its packaging, which is in the nature of a cradle. This cradle is useful for retaining a calibration body against the optical window of the probe, permitting a new probe to be calibrated even before its packaging is removed.

The fluorescence pattern applied to the calibration body 510 contains any suitable and preferably non-toxic fluorophore or combination of fluorophores. The ideal fluorophore is inexpensive, bright, capable of yielding calibration information over all response wavelengths of interest, non-toxic and safe, compatible with sterilization techniques, and capable of being incorporated in any desired pattern on a substrate. Other fluorophores not approved as non-toxic and safe can be used provided they are held out of contact with sterile external surfaces, whether by a barrier material or a gap. One suitable fluorophore material is fluorescent microspheres, which are small polystyrene spheres about 1 or 2 microns in diameter coated with highly fluorescent material and placed in solution, typically a latex suspension. One variety is made by Polysciences, Inc. of Warrington, Pa. under the tradename "Fluoresbrite Carboxylate," and is available at various emissions wavelengths across the entire ultraviolet to infrared spectrum. Another suitable fluorophore material is fluorescent dyes, which tend to have similar fluorescence spectral ranges. Suitable new fluorescent dyes having molar extinction coefficients and quantum yields superior to common fluorophores include Dansyl Aziridine and related groups R—$NH_2$, Lucifer Yellow, Aminomethylcoumarin, "NBD," Coumarin Iodoacetamide, Eosin, Erythrosin, and Erythrosin Aminomethylcoumarin. These dyes are available from Molecular Probes, Inc. of Eugene, Oreg. Suitable more common fluorescent dyes include Rhodamine, Indocyanine Green, Fluorescein (approved by the FDA for use as a food coloring), Fluorescein Isothiocyanate (FITC), Phycoerythrin, Ethidium Bromide, Texas Red, Cascade Blue, Dansyl Chloride, NBD Chloride, and the like. These dyes are available from a variety of manufacturers, including Molecular Probes, Inc. of Eugune, Oreg.; Excitron, Inc. of Dayton, Ohio; and Molecular Dynamics of Sunnyvale, Calif.

Figure 7:
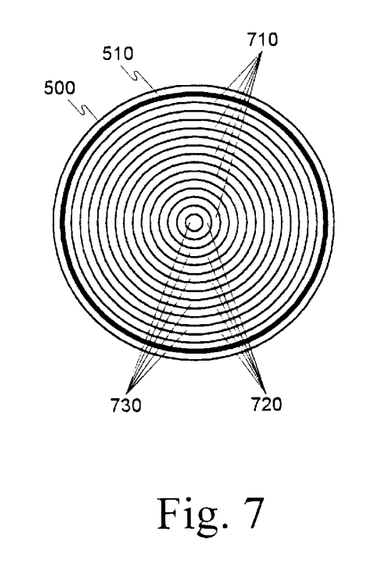
FIG. 7 shows a calibration body having a pattern of three fluorophores.

The fluorophores are applied to the calibration body 510 in any suitable manner, including inks that are painted, printed, sprayed or vacuum deposited onto the calibration body 510, solutions containing one or more fluorescent microspheres that are painted, printed, sprayed or vacuum deposited onto the calibration body 510, solids such as polymers that are laid on or molded to the calibration body 510, dopants that are absorbed or diffused into or otherwise incorporated into the calibration body 510, or other materials that are otherwise applied to the calibration body 510. The detection methods described in, for example, the aforementioned Richards-Kortum et al. patent documents uses preferably the excitation wavelengths of 337 nm, 380 nm, and 460 nm to provide multiple emission wavelengths, and preferably calibrates on a pattern that is fluorescent at each of the excitation wavelengths. One technique for achieving such a pattern is to apply a mixture of microspheres or fluorophores for each of the excitation wavelengths to the entire surface of the calibration body 510 within the field of view of the probe, wherein the microspheres or fluorophores used provide preferably a constant intensity field over the entire field of view. A mixture of the following types of microspheres from Polysciences, Inc. is illustrative: type BB excites at 365 nm and emits at 468 nm (medium blue); type YG excites at 458 nm and emits at 540 nm (green); type YO excites at 530 nm and emits at 590 nm (dark yellow); and type PC Red excites at 591 nm and emits at 657 nm (red). A similar fluorescent spectrum can be attained from more common non-microsphere dyes by substituting Coumarin, Fluorescein, Rhodamine, and Phycoerythrin for BB, YG, YO, and PC Red. Alternatively, two or more fluorophores may be applied to the calibration body 510 in any suitable pattern, each fluorophore being fluorescent at a subset of one or more of the excitation wavelengths used in the detection method to provide collectively multiple emission wavelengths from a plurality of excitation wavelengths. For example, as shown in FIG. 7, three fluorophores 710, 720 and 730 are applied in concentric rings, each of the fluorophores 710, 720 and 730 providing preferably a constant intensity field in the areas of the calibration body 510 to which it is applied. Other predetermined patterns and random distribution patterns may be used if desired.

Figure 8:
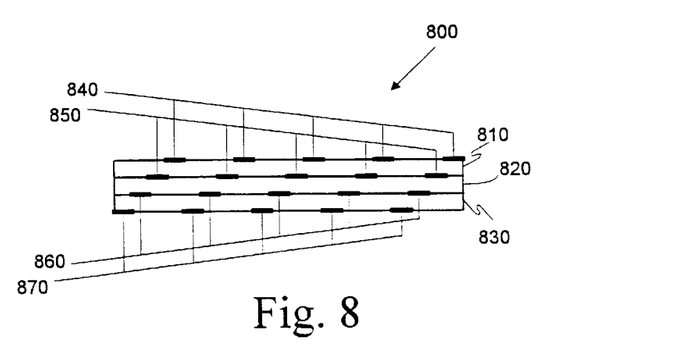
FIG. 8 shows a multiple-layer calibration body having multiple fluorophore patterns at different depths of field.

A variety of materials are suitable for the calibration body 510, depending on the manner in which the fluorophores are applied. For example, where fluorophores are painted, printed, sprayed or vacuum deposited onto the calibration body 510, suitable materials include metallic foils such as aluminum or copper, and lead foil may also be suitable if protection of the calibration strip from the effects of sterilization is necessary. Where fluorophores are laid on or molded into the calibration body 510, suitable materials include fluorescent coated microspheres such as the "Fluoresbrite Carboxylate" microspheres available from Polysciences, Inc. Where fluorophores are dopants that are absorbed into or otherwise incorporated into the calibration body 510, suitable materials include the common fluorophores such as Coumarin Fluorescein, Rhodamine, Phycoerythrin, Ethidium Bromide, and Texas Red.

Where the detection method requires calibration at different depths of field, the fluorophores are embedded in a multiple layer calibration body. For example, FIG. 8 shows a calibration body 800 having three layers 810, 820 and 830. Respective fluorophore patterns 840, 850, 860 and 870 are disposed at the interfaces of the layers 810, 820 and 830, at different depths of field. Suitable materials for the layers 810, 820 and 830 include Coumarin Fluorescein, Rhodamine, Phycoerythrin, Ethidium Bromide, and Texas Red.

Figure 9:
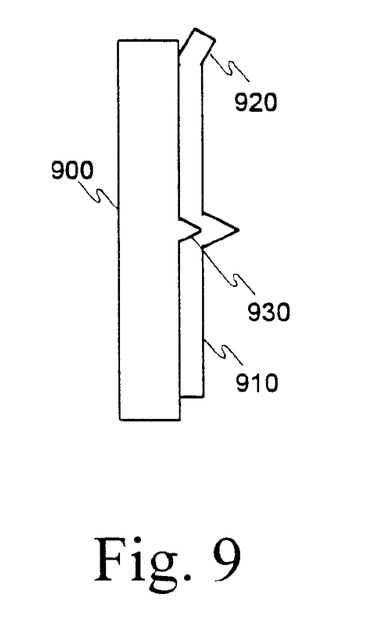
FIG. 9 is a cross-sectional view of a calibration body disposed on an optical window having a central conical protrusion.
Figure 10:
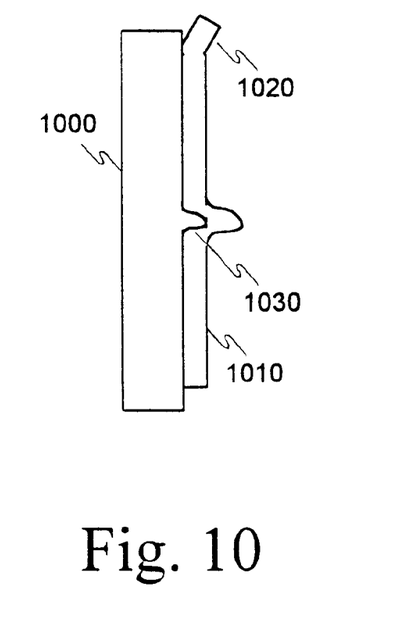
FIG. 10 is a cross-sectional view of a calibration body disposed on an optical window having a central contoured protrusion.

The calibration body 510 preferably is contoured to match the shape of the optical window 500. The optical window 500 shown in FIG. 5 is flat, so preferably the calibration body 510 is also flat. A tab 520 extending from the calibration body 510 may be provided, if desired, to facilitate removal of the calibration body 510. In the alternative optical window shapes shown in FIGS. 9 and 10, centrally located conical protrusion 930 and contoured protrusion 1030 respectively help locate the probe at the center of the cervix. The compound shape of the contoured protrusion 1030 in the optical window 1000 is patterned after the shapes used in various cryogenic probes that are used to treat the cervix. The protrusions 930 and 1030 preferably are made of the same material as the optical windows 900 and 1000, and either are formed from the same piece or are attached to a flat window element. Optical energy is emitted from the surface of optical windows 900 and 1000, including from the surfaces of the protrusions 930 and 1030, and the calibration bodies 910 and 1010 match the contour of the optical windows 900 and 1000. Contour matching is accomplished by providing the calibration bodies 910 and 1010 with pre-molded contours, or by using a stretchable material for their manufacture, or a plastic (capable of being shaped or formed) material such as a non-toxic and sterile clay or gel that is either non-adherent to the optical window and does not leave a residue or is biologically inert and non-interfering with the detection method. Suitable stretchable substrate materials include new hypoallergenic polymers such as nitrites as well as common latex and silicone.

Figure 11:
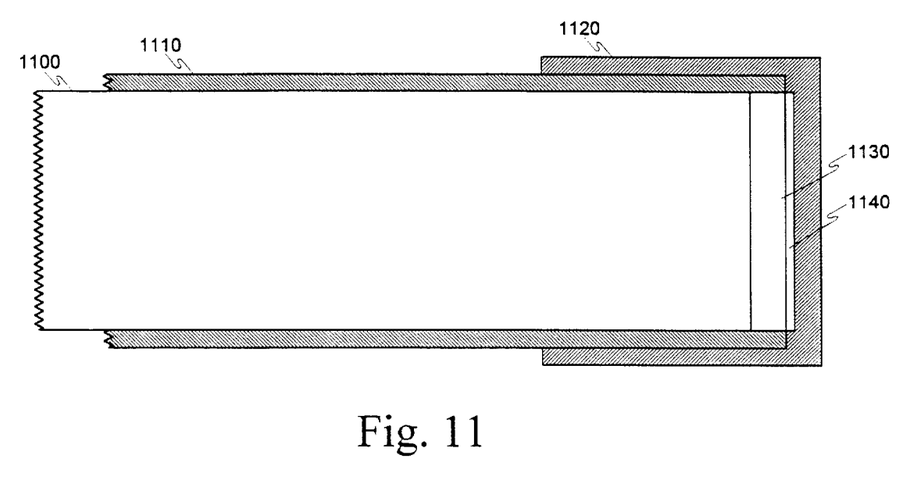
FIG. 11 is a side view of a light masking arrangement in which a calibration body is contained in an endcap that fits over the optical window of a probe.

Any suitable technique may be used to maintain the calibration body in a fixed position in the field of view of the probe. For example, in the arrangement shown in FIG. 6, the optical window 500 may be rigid or flexible, and the calibration body 510 is a flexible disk held to the optical window 500 with a non-fluorescing, low tear-strength, and low residual adhesive that is non-toxic and leaves no appreciable residue on the optical window 500 when the calibration body 510 is removed. Suitable adhesives include medical and industrial quality silicone, acrylic and rubber. Silicone adhesives have very good humidity and temperature resistance (about 600° F.), and are especially superior at high temperatures. Acrylic adhesives have good humidity and temperature resistance (about 300° F.), and are also quite stable chemically to such materials as solvents and oils. Adhesives with a low shear strength are available from a number of vendors, including the 3M Company of Minneapolis, Minn., and the Avery Dennison Company of Framingham, Mass. Alternatively, where the optical window 500 is rigid, the calibration body 510 may be pressed against the optical window 500 by the use of a conformal resilient cap (not shown) that engages the edge of the optical window 500 and is easily removable after calibration is completed, or by the use of a conformal cap of shrink-wrap plastic (not shown) that is suitably perforated for easy tear off after calibration is completed, or the use of an adhesive-backed foil tape that is applied over the calibration body 510 and engages exposed regions of the optical window 500. In another alternative particularly suitable for use with rigid sheaths such as sheath 410 of FIG. 4, the calibration body is attached to or integrated into a secondary probe cover which is generally conformal with the optical end of the probe and engages the optical end of the probe in any suitable manner, preferably without adhesive. For example, FIG. 11 shows a rigid sheath 1110 installed on a probe 1100. A rigid endcap 1120 is press-fitted on the end of the sheath 1110, which is over the optical end of the probe 1100. The sheath 1110 includes an optical window 1130, and the endcap 1120 includes a calibration pattern 1140 which is held flush against the optical window 1130.

Similarly, any suitable technique may be used to maintain the calibration body in a fixed position in the field of view of the probe even where a sheath is not used in the calibration process and the optical window of the probe is an orifice. For example, the calibration body 510 may be suspended in the field of view of the probe by being applied to a conformal resilient cap that engages the probe tip and is easily removable after calibration is completed, or to a conformal cap of shrink-wrap plastic that is suitably perforated for easy tear off after calibration is completed, or to an adhesive-backed foil tape that is applied over the probe tip, or by the use of a spring, preferably a plastic spring, that is compressed along the diameter of the probe tip.

Figure 12:
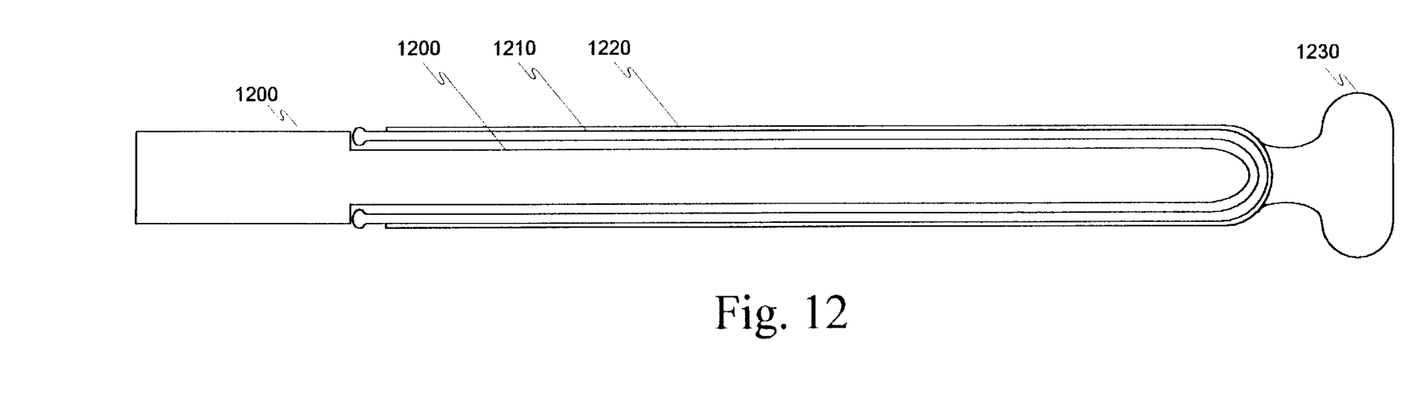
FIG. 12 is a cross-sectional view of a long thin probe having a tear-off calibration body.
Figure 13:
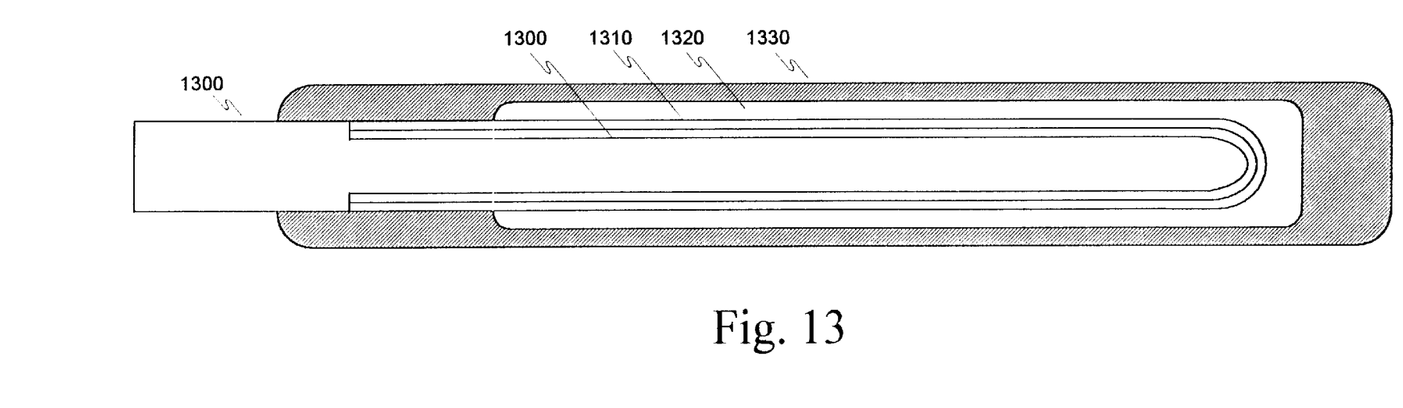
FIG. 13 is a cross-sectional view of a long thin probe having a gel-like calibration body maintained in place by a cap.

FIGS. 12 and 13 show exemplary techniques for maintaining a calibration body in a fixed position in the field of view of a long thin probe such as might be used in tubular or ductal anatomical structures such as, for example, the artery, vein, ureter, urethra, endocervical canal vagina, and ovarian duct. Illustratively, the probes 1200 and 1300 are generally cylindrical and rigid side-looking endocervical probes of less than about 3 mm in diameter, including, for example, spot probes, ring probes, line probes, and area probes as disclosed in U.S. patent application Ser. No. 08/693,471, filed Aug. 2, 1996 by Dr. Rebecca Richards-Kortum, Dr. Michele Follen Mitchell, and Dr. Urs Utzinger and entitled "Method and Apparatus for the Characterization of Tissue of Epithelial Lined Viscus" which is hereby incorporated herein by reference in its entirety. However, it will be appreciated that the techniques described are not limited to such probes. Where the probes 1200 and 1300 are ring, line or spot type probes which are moved along their longitudinal axis or rotated about their longitudinal axis or both to obtain a suitable number of measurements throughout the endocervical canal, the probes 1200 and 1300 preferably are operated within respective tubes 1210 and 1310, which are inserted into the endocervical canal and maintained in place during the measurement period. Where the probes 1200 and 1300 are area probes, they may be used with or without the tubes 1210 and 1310; if used without, the calibration techniques described herein are practiced directly on the probes 1200 and 1300.

The probe 1200 is calibrated using a calibration body 1220, which is any suitable material such as foil, plastic, nitrile, latex and silicone which envelopes the tube 1210 and carries a fluorescence pattern at least in the detection area of the probe 1200, which is typically near its tip. The tube 1210 and calibration body 1220 preferably are packaged as a sterile unit. The probe 1200 is calibrated by inserting it into the tube 1210 and performing the calibration operation. Once calibration is completed, the calibration body 1220 is torn off using the tab 1230 and discarded, the probe 1200 is removed from the tube 1210, the tube 1210 is inserted into the endocervical canal, the probe 1200 is inserted into the tube 1210, and measurements are taken. When investigation of the cervix is completed, the probe 1200 is removed from the tube 1210, and the tube 1210 is removed from the endocervical canal and suitably disposed of. Alternatively, where the tube 1210 is not used, the calibration body may be packaged with a resilient sheath as a sterile unit (not shown), and may be integral with the sheath or removable therefrom.

The sheath, including the calibration body, is pulled over the probe, which is then calibrated. Once calibration is completed, the calibration body is removed from the sheath and the sheath-covered probe is inserted into the endocervical canal, or the sheath and integrated calibration body are removed and the suitably sterile probe is inserted into the endocervical canal. Measurements are taken, the probe is removed from the endocervical canal, and if present, the sheath is removed and suitably disposed of. Alternatively, where the tube 1210 is not used, the calibration body may be a gel, clay or lining inside portions of a cap like the cap 1330 shown in FIG. 13. The probe is inserted into the cap and is calibrated. Once calibration is completed, the probe is removed from the cap and inserted into the endocervical canal. Measurements are taken and the probe is removed from the endocervical canal.

The probe 1300 is calibrated using a resilient cap of 1330 any suitable material which envelopes the tube 1310 and forms a cavity about the probe 1300 at least in the detection area thereof, which is typically near its tip. A suitable calibration body 1320 such as, for example, a fluorescent gel fills the cavity. Alternatively, a clay may be used, or the inside of the cap may be lined with fluorescent material. The tube 1310, calibration body 1320, and cap 1330 form a coaxial structure that is packaged as a sterile unit. The probe 1300 is calibrated by inserting it into the coaxial structure, attaching the coaxial structure to the probe 1300 by using, for example, a twist-type mount on the tube 1310 or any other suitable type of mount, and performing the calibration operation. Once calibration is completed, the cap 1330 is slid off the tube 1310 with calibration body 1320 and discarded, the probe 1300 is removed from the tube 1310, the tube 1310 is inserted into the endocervical canal, the probe 1300 is inserted into the tube 1310, and measurements are taken. When investigation of the cervix is complete, the probe 1300 is removed from the tube 1310, and the tube 1310 is removed from the endocervical canal and suitably disposed of. Alternatively, where the probe 1300 is an area probe, the tube 1310 with the probe 1300 attached may be inserted into and removed from the endocervical canal as a unit.

In some applications, the ambient light or other external light source may be used to excite the fluorophores or other material in the calibration body, or the illumination may be made through a different optical window than through which the returning optical energy emitted by the calibration body is detected. The detection system runs the calibration sequence based on the detected returns.

For applications in which the detection system is designed to detect weak tissue autofluorescence or other weak returns from the body cavity tissue, the fluorophores used in the calibration pattern preferably are weak to mimic the magnitude of the autofluorescence expected from the fluorescence spectroscopy. In this case, or in cases in which the ambient light may interfere with the wavelengths of the returns, opaque or reflective materials are used to shield the optical end of the probe from ambient light that would otherwise interfere with accurate calibration. For example, in the arrangement of FIG. 11, the sheath 1110 is provided with a region (cross-hatched) that is opaque to the illuminating and return wavelengths, and the entire cap 1120 (cross-hatched) but for the calibration region 1140 is also opaque to the illuminating and return wavelengths. The endcap 1120 firmly engages the sheath 1110 over a length sufficient to block ambient light from entering the field of view of the probe 1100.

Figure 14:
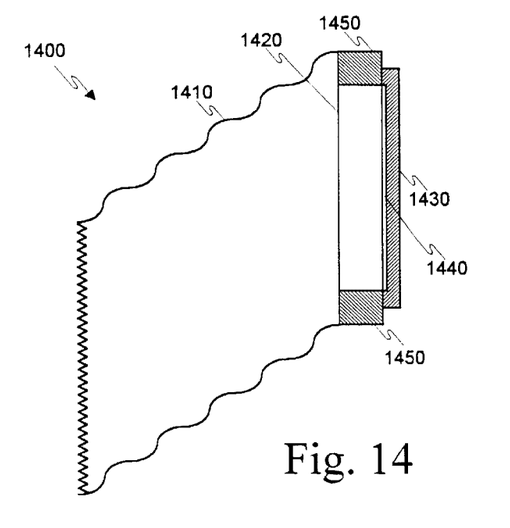
FIG. 14 is a side view of a light masking arrangement in which a calibration body is held in place over the optical window of a probe by an adhesive.

Similar light masking techniques are used to adapt other calibration body attachment techniques to situations in which low magnitude returns are expected. For example, as shown in FIG. 14, the sheath 1400 may be furnished with an opaque or reflective tubular member 1410 otherwise similar to the tubular member 210, and an optical window 1420 which is similar to the optical window 220 but is provided with a mask 1450 of opaque material over the edges and front except for portions in the field of view of the probe with which the sheath 1400 is used. Calibration body 1430 having a calibration pattern 1440 is applied to the optical window 1420 with a suitable adhesive or held in place by a suitable conformal shrink-wrap material (not shown) or conformal endcap (not shown). The calibration body 1430 is similar to calibration body 510 of FIG. 6 except that it is made opaque to the illuminating and return wavelengths, and overlaps the optical window mask 1450 when in place on the optical window 1420. Where a suitable conformal shrink-wrap material or conformal endcap is used, it may also be made opaque to the illuminating and return wavelengths in addition to or instead of making the calibration body opaque.

If desired, portions of the calibration body may carry a code containing information useful to the detection system such as specific calibration factors, operating parameters, expiration date codes, and system upgrade notifications. Preferably, the code is a bar code or other suitable grid pattern. Alternatively, or additionally, the code may contain identification information or security information in encrypted form for legitimizing the use of the detecting system with the particular disposable to ensure compatibility and quality, and to ensure safety by preventing reuse. Where supported, the code is read by the detection system and suitably processed.

If desired, the calibration body may include additional materials to ensure single use thereof. For example, the calibration body may contained dispersed microencapsulated materials which rupture when the calibration body is removed. The rupturing of the microencapsulated materials releases materials that interfere with the calibration procedure or otherwise causes degeneration of the surfaces such that the calibration body or its packaging cannot be reused. Suitable materials include fragile polymer films laminated as pouches located inside and laminated to suitable rugged external material. The more fragile layers containing the fluorophores are designed to rupture upon removal of the calibration strip, thereby dispersing the fluorophores in a spatial distribution unsuitable for calibration. Alternatively, the calibration strip may contain material that causes the calibration strip, including if desired any bar code or encrypted data thereon, to bleach or darken, to become abraded, or otherwise to degrade when exposed to illuminating energy during the calibration sequence. Suitable materials include various commercially available formulations of selected short-lifetime, photobleaching fluorophores such as Rhodamine Fluorophores applied to microspheres. Photobleaching dyes such as Fluorescein and Rhodamine are available from a variety of manufacturers, including Molecular Probes, Inc. of Eugene, Oreg.

Calibration of the detecting system is performed in any suitable manner. Illustratively, the emission wavelength of interest is detected and intensity variations are removed by automated calibration circuitry in the instrument. Scaling factors are generated electronically by scanning the output of the detector under the controlled fluorescence generated by the calibration strip. These factors are used to selectively amplify or attenuate each image element which is sensed by the detectors. This produces an amplitude-corrected signal which is calibrated from the incident light through the return light to the detector output signal, which is supplied to the algorithm-computational elements of the processor. In the event that the automatic calibration sequence fails to compensate for the intensity variations, the fault is assumed to be in the probe and a probe failure signal is generated. The probe should at that time be removed from service and independently tested.

The techniques described to this point are useful with instruments that use filters to measure the emission intensity as well as systems that use spectrometers to measure the emission intensity. While the techniques provide a complete calibration source for systems that use filters, spectrometer-based systems typically require additional calibration techniques containing wavelength information.

The description of the invention set forth herein is illustrative, and does not limit the scope of the invention as set forth in the following claims. Variations and modifications of the embodiments disclosed herein are possible. For example, while the calibration techniques described herein are particularly advantageous when used in conjunction with a sheath as a disposable unit, the calibration techniques are not limited to this application. For instance, the calibration bodies described herein may be applied directly to the probe or to packaging material for the probe or for the sheath, or may be incorporated into a separate calibration apparatus such as a probe cradle or into a calibration phantom. Moreover, while the description to this point has dwelt on in vivo applications, the techniques described above are equally applicable to probes used for in vitro applications. Moreover, while the description to this point has focused on fluorescence systems, the techniques described above are equally applicable to probes used with other systems that are based on Raman scattering, for example, or that use different wavelengths in the infrared, ultraviolet, and x-ray ranges, for which other calibration dyes or materials may be suitable. Moreover, while the description to this point has dwelt on fluorophores, other materials such as various chromophores having unique sensitivity and amplitude of response in the spectroscopic region of interest may also be used, as well as other substances having suitable scintillation properties. These and other variations and modifications of the embodiments disclosed herein may be made without departing from the scope and spirit of the invention.

What is claimed is:

1. A self-calibrating autofluorescence tissue probe apparatus comprising:

an optical probe having a reusable section and a disposable section, the disposable section having an optical window that is transparent to optical energy at first and second wavelengths, the optical window being a rigid body;

a substrate coupled to the optical probe and removably disposed in a field of view of the optical window, the substrate being rigid and disposed against the optical window; and a fluorescent material that is excitable by optical energy at the first wavelength to become fluorescent at the second wavelength, the fluorescent material being supported by the substrate in the field of view of the optical window;

wherein the optical window is a lens having a contoured external surface and the substrate has a contoured inside surface adjacent and matching the contoured external surface of the optical window.

2. A self-calibrating autofluorescence tissue probe apparatus comprising:

an optical probe having a reusable section and a disposable section, the disposable section having an optical window that is transparent to optical energy at first and second wavelengths and comprising a flexible sheath comformable with at least a portion of the reusable section of the optical probe, the optical window being a rigid optical body integral with the flexible sheath and the substrate being disposed on the rigid optical body;

a substrate coupled to the optical probe and removably disposed in a field of view of the optical window; and a fluorescent material that is excitable by optical energy at the first wavelength to become fluorescent at the second wavelength, the fluorescent material being supported by the substrate in the field of view of the optical window.

3. A self-calibrating autofluorescence tissue probe apparatus comprising:

an optical probe having a reusable section and a disposable section, the reusable section of the optical probe comprising a rigid optical window at a distal end thereof, and the disposable section having an optical window that is transparent to optical energy at first and second wavelengths and comprising a flexible sheath comformable with at least a portion of the reusable section of the optical probe, the optical window being integral with the sheath and having a first surface and a second surface opposing the first surface, the first surface being disposed against the rigid optical window of the reusable section of the optical probe and the substrate being disposed on the second surface;

a substrate coupled to the optical probe and removably disposed in a field of view of the optical window; and a fluorescent material that is excitable by optical energy at the first wavelength to become fluorescent at the second wavelength, the fluorescent material being supported by the substrate in the field of view of the optical window.

4. A self-calibrating autofluorescence tissue probe apparatus comprising:

an optical probe having a reusable section and a disposable section, the disposable section having an optical window that is transparent to optical energy at first and second wavelengths and comprising a rigid sheath in removable engagement with at least a portion of the reusable section of the optical probe, the optical window being a rigid optical body integral with the sheath and the substrate being disposed on the rigid optical body;

a substrate coupled to the optical probe and removably disposed in a field of view of the optical window; and a fluorescent material that is excitable by optical energy at the first wavelength to become fluorescent at the second wavelength, the fluorescent material being supported by the substrate in the field of view of the optical window.

5. A self-calibrating autofluorescence tissue probe apparatus comprising:

an optical probe having a reusable section and a disposable section, the reusable section of the optical probe comprising a rigid optical window at a distal end thereof, and the disposable section having an optical window that is transparent to optical energy at first and second wavelengths and comprising a rigid sheath in removable engagement with at least a portion of the reusable section of the optical probe, the optical window being integral with the sheath and having a first surface and a second surface opposing the first surface, the first surface being disposed against the rigid optical window of the reusable section of the optical probe and the substrate being disposed on the second surface;

a substrate coupled to the optical probe and removably disposed in a field of view of the optical window; and a fluorescent material that is excitable by optical energy at the first wavelength to become fluorescent at the second wavelength, the fluorescent material being supported by the substrate in the field of view of the optical window.

6. A self-calibrating autofluorescence tissue probe apparatus comprising:

an optical probe having a reusable section and a disposable section, the disposable section having an optical window that is transparent to optical energy at first and second wavelengths;

a substrate coupled to the optical probe and removably disposed in a field of view of the optical window;

an optical mask disposed about the substrate and the optical window; and a fluorescent material that is excitable by optical energy at the first wavelength to become fluorescent at the second wavelength, the fluorescent material being supported by the substrate in the field of view of the optical window.

7. A self-calibrating autofluorescence cervical tissue probe comprising:

a generally cylindrical elongated optical probe having an optical window at one end that is transparent to optical energy at plural illuminating wavelengths and at plural return wavelengths;

a generally circular substrate coupled to the optical probe and removably disposed in a field of view of the optical window;

fluorescent material that is excitable by optical energy at the illuminating wavelengths to become fluorescent at the return wavelengths, the fluorescent material being supported by the substrate in a field of view of the optical window;

a single-use material supported by the substrate in the field of view of the optical window; and an optical mask disposed about the substrate and the optical window.

8. An apparatus as in claim 7 wherein the fluorescent material comprises fluorescent microspheres disposed on the substrate.

9. An apparatus as in claim 8 wherein the fluorescent microspheres are coated with a variety of fluorophores having respective excitation wavelengths.

10. An apparatus as in claim 7 wherein the fluorescent material comprises a fluorescent dye that is disposed on the substrate.

11. An apparatus as in claim 7 wherein the fluorescent material comprises a mixture of fluorescent dyes that are disposed on the substrate and have respective excitation wavelengths.

12. A method for calibrating a tissue analysis system that includes an optical probe having an optical window transparent to a return wavelength, the optical window having a field of view, the method comprising:

positioning a calibration body in the field of view of the optical window;

illuminating the calibration body at an illuminating wavelength to excite material distributed in the calibration body, the excited material emitting energy at a return wavelength in a predetermined pattern across a region of the calibration body;

detecting the energy at the return wavelength through the optical window in accordance with a set of scaling factors;

deciding whether the predetermined pattern is present from the energy detected in the detecting step; and in the event that the predetermined pattern is found to be not present in the deciding step, adjusting the set of scaling factors and repeating the illuminating, detecting, and deciding steps.

13. A method as in claim 12 wherein the illuminating step is performed through the optical window, the optical window being transparent to the illuminating wavelength.

14. A method as in claim 12 further comprising the step of indicating a defect in the event that the predetermined pattern is found to be not present in the deciding step after a predetermined number of repetitions of the deciding step.

15. A method for calibrating a tissue analysis system that includes an optical probe having an optical window transparent to first and second sets of return wavelengths, the optical window having a field of view, the method comprising:

positioning a calibration body in the field of view of the optical window;

illuminating the calibration body at a first illuminating wavelength to excite material distributed in the calibration body, the excited materials emitting energy at the first set of return wavelengths in a first predetermined pattern across a region of the calibration body;

illuminating the calibration body through the optical window at a second illuminating wavelength to excite material distributed in the calibration body, the excited material emitting energy at the second set of return wavelengths in a second predetermined pattern across a region of the calibration body;

detecting the energy at the first and second sets of return wavelength through the optical window in accordance with, respectively, first and second sets of scaling factors;

deciding whether the first and second predetermined patterns are present from the energy detected in the detecting step; and in the event that the predetermined pattern is found to be not present in the deciding step, adjusting the first and second sets of scaling factors and repeating the illuminating, detecting, and deciding steps.

16. A method as in claim 15 wherein the illuminating step is performed through the optical window, the optical window being transparent to the first and second illuminating wavelengths.

17. A method as in claim 15 further comprising the step of indicating a defect in the event that any one of the first and second predetermined patterns is found to be not present in the deciding step after a predetermined number of repetitions of the deciding step.

18. A method for calibrating a tissue analysis system that includes an optical probe having an optical window transparent to a return wavelength, the optical window having a field of view, the method comprising:

positioning a calibration body in the field of view of the optical window;

applying optical energy to the calibration body, the optical energy interacting with material distributed in the calibration body to return energy at a return wavelength in a predetermined pattern across a region of the calibration body;

detecting the energy at the return wavelength through the optical window in accordance with a set of scaling factors;

deciding whether the predetermined pattern is present from the energy detected in the detecting step; and in the event that the predetermined pattern is found to be not present in the deciding step, adjusting the set of scaling factors and repeating the applying, detecting, and deciding steps.

19. A method as in claim 18 wherein the applying step is performed through the optical window.

20. A method as in claim 18 further comprising the step of indicating a defect in the event that the predetermined pattern is found to be not present in the deciding step after a predetermined number of repetitions of the deciding step.

21. A disposable sheath for use with a reusable optical body cavity probe section, comprising:

an elongated member of a length and cross-section suitable for insertion into the body cavity;

an optical window having a field of view disposed in the elongated member, the optical window comprising a rigid lens; and a body removably disposed in the field of view of the optical window and containing fluorescent material distributed in a predetermined pattern across a region of the body, the fluorescent material being excitable by optical energy at a first wavelength to become fluorescent at a second wavelength in a predetermined pattern across the body region.

22. A disposable sheath for use with a reusable optical body cavity probe section, comprising:

an elongated member of a length and cross-section suitable for insertion into the body cavity;

an optical window having a field of view disposed in the elongated member, the optical window comprising a flexible optical body; and a body removably disposed in the field of view of the optical window and containing fluorescent material distributed in a predetermined pattern across a region of the body, the fluorescent material being excitable by optical energy at a first wavelength to become fluorescent at a second wavelength in a predetermined pattern across the body region.

23. A disposable sheath for use with a reusable optical body cavity probe section, comprising:

an elongated member of a length and cross-section suitable for insertion into the body cavity, the elongated member comprising a flexible sheath;

an optical window having a field of view disposed in the elongated member; and a body removably disposed in the field of view of the optical window and containing fluorescent material distributed in a predetermined pattern across a region of the body, the fluorescent material being excitable by optical energy at a first wavelength to become fluorescent at a second wavelength in a predetermined pattern across the body region.

24. A disposable sheath for use with a reusable optical body cavity probe section, comprising:

an elongated member of a length and cross-section suitable for insertion into the body cavity;

an optical window having a field of view disposed in the elongated member; and a body removably disposed in the field of view of the optical window and containing fluorescent material distributed in a predetermined pattern across a region of the body, the fluorescent material being excitable by optical energy at a first wavelength to become fluorescent at a second wavelength in a predetermined pattern across the body region;

wherein the elongated member is elongated along a major axis and the optical window passes optical energy in a direction generally transverse to the major axis of the elongated member.

* * * * *